United States Patent
Oi et al.

(10) Patent No.: US 6,861,562 B2
(45) Date of Patent: Mar. 1, 2005

(54) PROCESS FOR PRODUCING MIXTURE OF DIHYDROXYDIPHENYLSULFONE ISOMERS

(75) Inventors: Fumio Oi, Wakayama (JP); Norio Yanase, Wakayama (JP); Hiroyuki Yamamoto, Wakayama (JP)

(73) Assignee: Konishi Chemical Ind. Co., Ltd., Wakayama (JP)

( * ) Notice: Subject to any disclaimer, the term of this patent is extended or adjusted under 35 U.S.C. 154(b) by 0 days.

(21) Appl. No.: 10/490,754
(22) PCT Filed: Sep. 26, 2002
(86) PCT No.: PCT/JP02/09918
§ 371 (c)(1), (2), (4) Date: Mar. 25, 2004
(87) PCT Pub. No.: WO03/029203
PCT Pub. Date: Apr. 10, 2003

(65) Prior Publication Data
US 2004/0242935 A1 Dec. 2, 2004

(30) Foreign Application Priority Data
Sep. 28, 2001 (JP) .......................... 2001-300946

(51) Int. Cl.$^7$ ............................................ C07C 315/04
(52) U.S. Cl. ................................ 568/34; 568/18; 568/27
(58) Field of Search ............................ 568/18, 27, 34

(56) References Cited

FOREIGN PATENT DOCUMENTS

| EP | 0 220 004 A1 | 4/1984 |
|---|---|---|
| EP | 0 461 272 A1 | 12/1991 |
| EP | 0 627 415 A1 | 12/1994 |
| EP | 0 755 920 A1 | 1/1997 |
| JP | 50-116446 A | 9/1975 |
| JP | 10-25277 A | 1/1998 |
| JP | 10-139756 A | 5/1998 |

*Primary Examiner*—Johann Richter
*Assistant Examiner*—Lansana Nyalley
(74) *Attorney, Agent, or Firm*—Knobbe, Martens, Olson & Bear LLP

(57) ABSTRACT

The present invention provides a process for producing a mixture of 4,4'- and 2,4'-dihydroxydiphenylsulfones comprising heating trihydroxytriphenyldisulfone or a mixture of dihydroxydiphenylsulfone isomers containing trihydroxytriphenyldisulfone in the presence of phenol and an acid catalyst.

7 Claims, No Drawings

PROCESS FOR PRODUCING MIXTURE OF DIHYDROXYDIPHENYLSULFONE ISOMERS

This application is the U.S. National Phase under 35 U.S.C. §371 of International Application PCT/JP02/09918, filed Sep. 26, 2002, which claims priority to Japanese Patent Application No. 2001-300946, filed September 28, 2001. The International Application was not published under PCT Article 21(2) in English.

TECHNICAL FIELD

The present invention relates to a process for producing a mixture of dihydroxydiphenylsulfone isomers containing 4,4'-dihydroxydiphenylsulfone (hereinafter occasionally referred to as 4,4'-DDS) and 2,4'-dihydroxydiphenylsulfone (hereinafter occasionally referred to as 2,4'-DDS).

BACKGROUND ART

Reactions for producing dihydroxydiphenylsulfone often generate trihydroxytriphenyldisulfone (hereinafter occasionally referred to as TTDS). Large amounts of TTDS are contained in the residue generated during purifying dihydroxydiphenylsulfone. TTDS is of little use and has been disposed of as a waste.

DISCLOSURE OF THE INVENTION

An object of the invention is to provide a process for producing a mixture of dihydroxydiphenylsulfone isomers by converting trihydroxytriphenyldisulfone to 4,4'-dihydroxydiphenylsulfone and 2,4'-dihydroxydiphenylsulfone, both of which have industrial utility.

Other objects and characteristics of the present invention will become evident by the disclosure provided hereinbelow.

The inventors conducted extensive research and found that TTDS heated in the presence of phenol and an acid catalyst is converted into 4,4'-DDS and 2,4'-DDS. The present invention has been accomplished based on this finding.

In other words, the present invention provides processes for producing a mixture of 4,4'- and 2,4'-dihydroxydiphenylsulfones:

1. A process for producing a mixture of 4,4'- and 2,4'-dihydroxydiphenylsulfones, the process comprising heating trihydroxytriphenyldisulfone in the presence of phenol and an acid catalyst.
2. A process for producing a mixture of 4,4'- and 2,4'-dihydroxydiphenylsulfones, the process comprising heating a mixture of dihydroxydiphenylsulfone isomers containing trihydroxytriphenyldisulfone in the presence of phenol and an acid catalyst.

Hereinbelow, the process for producing a mixture of dihydroxydiphenylsulfone isomers of the present invention is described in more detail:

TTDS used as a starting material of the invention is represented by Formula (1):

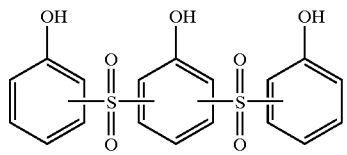

As a starting material, a mixture of dihydroxydiphenylsulfone isomers containing TTDS can also be used. Isomers of dihydroxydiphenylsulfone include 4,4'-DDS and 2,4'-DDS. This isomeric mixture can be crude dihydroxydiphenylsulfone obtained during the production of dihydroxydiphenylsulfone.

The starting material, i.e., TTDS or a mixture of dihydroxydiphenylsulfone isomers containing TTDS is converted into 4,4'-DDS and 2,4'-DDS by heating in the presence of phenol and an acid catalyst.

Phenol is used preferably in a weight of no more than twice as much as, and more preferably in a weight of 0.1 to 1 times as much as, the starting material, i.e., TTDS or a mixture of dihydroxydiphenylsulfone isomers containing TTDS. However, since phenol can function also as a reagent, it is preferably used in a weight of no less than 0.23 times as much as TTDS.

Examples of acid catalysts usable in the invention include benzenetrisulfonic acid, benzenedisulfonic acid, chlorobenzenedisulfonic acid, toluenesulfonic acid, phenolsulfonic acid, and like aromatic mono-, di-, or trisulfonic acids; methanesulfonic acid, ethanesulfonic acid, trifluoromethanesulfonic acid, pentafluoroethanesulfonic acid, and like optionally-fluorinated aliphatic sulfonic acids; Nafion® and like polymeric sulfonic acids; sulfuric acid and like inorganic acids; etc. Among these acid catalysts, aromatic mono-, di-, trisulfonic acids and inorganic acids are preferable; and benzenedisulfonic acid, sulfuric acid, and the like are more preferable.

The acid catalyst is used preferably in a proportion of 20 mol % or lower, and more preferably in a proportion of 1 to 10 mol %, based on the starting material, i.e., TTDS or a mixture of dihydroxydiphenylsulfone isomers containing TTDS.

Solvents may or may not be used. When solvents are used, heat- and acid-resistant solvents such as sulfolane and the like are preferable.

The reaction temperature is preferably 160° C. or higher, and more preferably 170 to 210° C. The reaction can be conducted under pressure as necessary.

The reaction time is not limited. It is preferably 0.1 to 20 hours, and more preferably 1 to 10 hours.

The desired product of the present invention, i.e., a mixture of 4,4'- and 2,4'-dihydroxydiphenylsulfones contains, in principle, substantially no TTDS. However, it can contain TTDS in an amount such that it does not hamper the separation and purification of 4,4'-DDS or 2,4'-DDS.

Moreover, even when the mixture contains TTDS, repeating the process of the invention can produce a mixture of dihydroxydiphenylsulfone isomers containing substantially no TTDS.

4,4'-DDS and 2,4'-DDS can be separated from a mixture of 4,4'- and 2,4'-dihydroxydiphenylsulfones produced according to the invention using known separation and purification methods.

The process of the present invention can produce a mixture of dihydroxydiphenylsulfone isomers by converting TTDS to 4,4'-DDS and 2,4'-DDS, both of which have industrial utility.

BEST MODE FOR CARRYING OUT THE INVENTION

Examples are given below to illustrate the invention in more detail.

EXAMPLE 1

To 100 g (0.25 mol) of TTDS were added 50 g of phenol and 3 g (0.01 mol, 4 mol % relative to TTDS) of benzenedisulfonic acid. The mixture was heated to 200° C. and stirred at this temperature. The results of HPLC (high performance liquid chromatography) analysis conducted after 2 hours of stirring revealed that the mixture contained 4,4'-DDS, 2,4'-DDS, and TTDS in a weight ratio of 33:13:54, the mixture after 6 hours of stirring contained 4,4'-DDS, 2,4'-DDS, and TTDS in a weight ratio of 64:21:15, and the mixture after 9 hours of stirring contained 4,4'-DDS, 2,4'-DDS, and TTDS in a weight ratio of 70:22:8.

EXAMPLE 2

To 100 g (0.38 mol) of a mixture of dihydroxydiphenylsulfone isomers containing 4,4'-DDS, 2,4'-DDS, and TTDS in a weight ratio of 75:13:12 were added 50 g of phenol and 3 g (0.03 mol, 8 mol % relative to the mixture) of 98% sulfuric acid. The mixture was heated to 200° C and stirred at this temperature. The results of HPLC analysis conducted after 2 hours of stirring revealed that the mixture contained 4,4'-DDS, 2,4'-DDS, and TTDS in a weight ratio of 75:19:6, the mixture after 6 hours of stirring contained 4,4'-DDS, 2,4'-DDS, and TTDS in a weight ratio of 74:24:2, and the mixture after 9 hours of stirring contained 4,4'-DDS, 2,4'-DDS, and TTDS in a weight ratio of 74:25:1.

What is claimed is:

1. A process for producing a mixture of 4,4'- and 2,4'-dihydroxydiphenylsulfones, the process comprising heating trihydroxytriphenyldisulfone in the presence of phenol and an acid catalyst.

2. A process for producing a mixture of 4,4'- and 2,4'-dihydroxydiphenylsulfones, the process comprising heating a mixture of dihydroxydiphenylsulfone isomers containing trihydroxytriphenyldisulfone in the presence of phenol and an acid catalyst.

3. A process for producing a mixture of 4,4'- and 2,4'-dihydroxydiphenylsulfones, comprising:

providing, as a starting material, trihydroxytriphenyldisulfone or a mixture of dihydroxydiphenylsulfone isomers containing trihydroxytriphenyldisulfone; and heating the starting material in the presence of phenol in an amount equal to or less than the starting material by weight and an acid catalyst in an amount of 20 mol % or less relative to the starting material, thereby obtaining a mixture of 4,4'- and 2,4'-dihydroxydiphenylsulfones.

4. The process according to claim 3, wherein the mixture of 4,4'- and 2,4'-dihydroxydiphenylsulfones contains substantially no trihydroxytriphenyldisulfone.

5. The process according to claim 3, wherein the phenol is used in an amount of no less than 0.23 times that of the starting material by weight.

6. The process according to claim 3, wherein the starting material is heated to 160° C. or higher.

7. The process according to claim 3, wherein the starting material is heated to 170–210° C. or higher.

* * * * *